Figure 1:
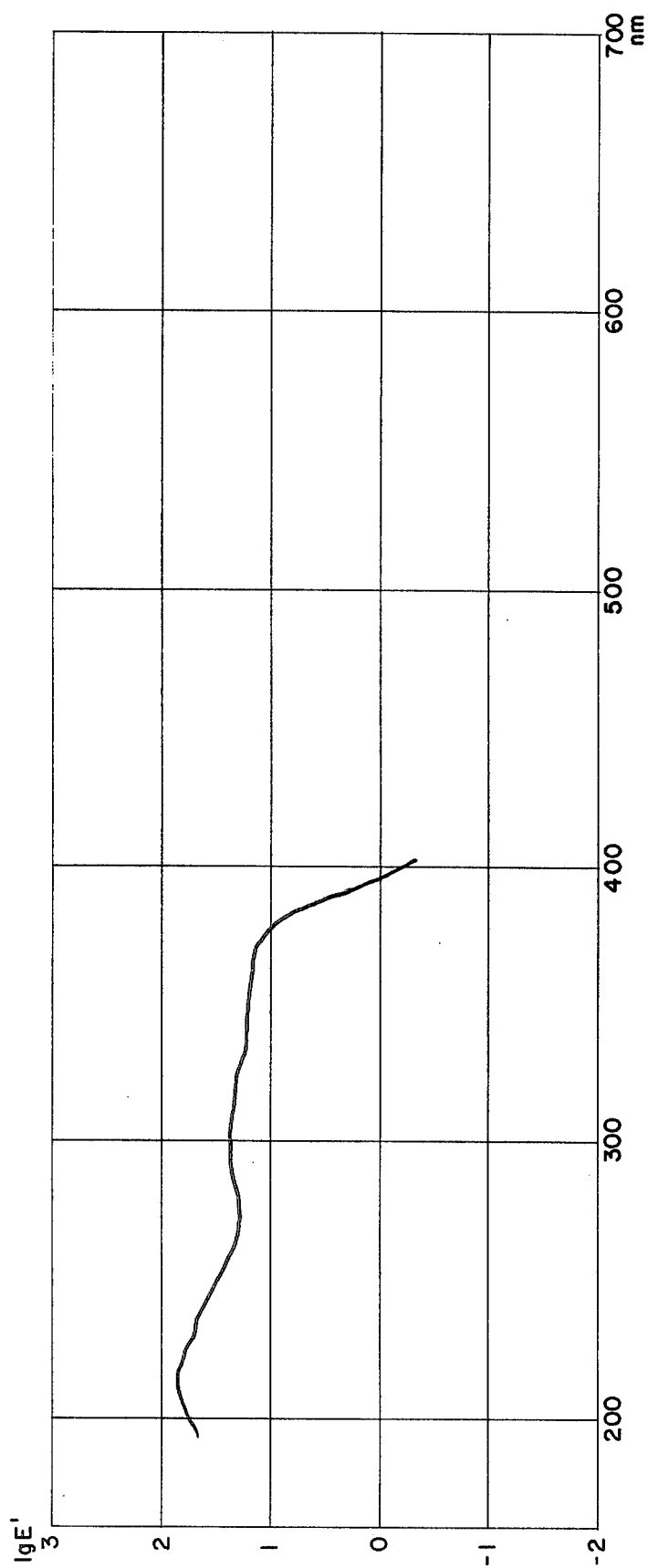

United States Patent [19]

Keller-Juslen et al.

[11] 4,216,206

[45] Aug. 5, 1980

[54] ANTIBIOTICS S 53210/A-I, S 53210/A-II AND S 53210/A-III

[75] Inventors: Camilla Keller-Juslen; Hamilton D. King, both of Basel, Switzerland

[73] Assignee: Sandoz Ltd., Basel, Switzerland

[21] Appl. No.: 4,804

[22] Filed: Jan. 19, 1979

Related U.S. Application Data

[63] Continuation-in-part of Ser. No. 917,770, Jun. 21, 1978, abandoned.

[30] Foreign Application Priority Data

Jun. 23, 1977 [CH] Switzerland .......................... 7716/77
Oct. 20, 1977 [CH] Switzerland ........................ 12795/77

[51] Int. Cl.² ..................... H61K 35/66; C12D 9/14
[52] U.S. Cl. ................................. 424/117; 435/169; 435/128; 435/822
[58] Field of Search ..................... 424/117; 195/80; 435/169

[56] References Cited

U.S. PATENT DOCUMENTS 4,083,963   4/1978   Celmer et al. ...................... 424/117

*Primary Examiner*—Jerome D. Goldberg
*Attorney, Agent, or Firm*—Gerald D. Sharkin; Robert S. Honor; Timothy G. Rothwell

[57] ABSTRACT

Antibiotics active against gram positive bacteria are produced from *Microellobosporia brunea* nov. Sp. King 1977.

7 Claims, 9 Drawing Figures

ANTIBIOTICS S 53210/A-I, S 53210/A-II AND S 53210/A-III

This is a continuation-in-part of our copending application No. 917,770, filed June 21, 1978, now abandoned.

The present invention relates to the antibiotics S 53210/A-I, S 53210/A-II and S 53210/A-III.

The present invention provides for the production of S 53210/A-I and/or S 53210/A-II and/or S 53210/A-III by cultivating a S 53210/A-I and/or S 53210/A-II and/or S 53210/A-III producing strain of Microellobospora on or in a culture medium and isolating S 53210/A-I and/or S 53210/A-II and/or S 53210/A-III therefrom.

The preferred new strain S 53210/A used in accordance with the invention was isolated from the soil scraped from an antique, approximately 2000 year-old clay head found in 1976 in Jama Coaque (Ecuador). A sample thereof was deposited with the United States Department of Agriculture, Peoria, Ill., USA on June 7, 1977 and is available as the culture No. NRRL 11, 122.

Owing to the fact that the strain S 53210/A initially only formed substrate mycelium with lateral single and double spores, it was assumed to belong to the genus Micromonospora. On some culture media however, the strain forms aerial mycelia after a two-week incubation and club-shaped, 2 to 7 $\mu$m long sporangia containing one to seven, globular to ellipsoidal, 1.0–2.7 $\mu$m large, non-motile spores. It appears that the spores are formed by septation of the short, club-shaped lateral branches; the individual spores enlarge in different ways, mature as a short chain in the sporangium and are released by an apical splitting of the sporangium. Long, streptomycete-like chains of spores have not been observed.

Owing to the above description, the strain S 53210/A corresponds well with the genus Microellobospora founded by Cross T., Lechevalier M. and Lechevalier H., 1963, A new genus of Actinomycetales: Microellobosporia gen. nov. Journ. Gen. Microbiology 31, 421 (1963). This genus embraces so far only four different strains (cf. Bergey's Manual of Determinative Bacteriology, 8 Edition, pages 843–845), with *M. cinerea* and *M. violacea* showing violet colours in the vegetative mycelium and the sporangia of *M. grisea* being covered with small crystalline spines. The strain S 53210/A does not show these marked characteristics. The fourth hitherto described strain, which does not produce any antibiotics, *M. flavea*, has according to the description a white aerial mycelium and forms straw-coloured colonies without soluble pigments. Thus the strain S 53210/A having a white aerial mycelium and beige to brown colonies without soluble pigments is very similar to this last strain. There are, however, considerable differences between *M. flavea* and the new strain S 53210/A as regards carbon utilization, e.g. the strain S 53210/A utilizes L-(+)-arabinose, D-(+)-raffinose and D-(+)-saccharose doubtfully while *M. flavea* utilizes these sugars completely. Further the utilization of D-(+)-maltose by the strain S 53210/A is very good in contrast to *M. flavea*.

Thus the strain S 53210/A is described to be a new species of the genus Microellobospora and is called *Microellobospora brunea*, nov. Sp. King, 1977, owing to its brown vegetative mycelium.

The growth properties of the strain S 53210/A on different culture media and its carbon assimilation are indicated in the following Tables:

| Medium | Cultural properties | Aerial mycelium form |
|---|---|---|
| Malt-yeast extract agar | G. : good, beige to brown substrate mycelium broken | appears after 16 days at the colony edges, Rectus flexibilis |
| | Und. : beige to brown | |
| | AM. : white, only at the colony edges, * white b | |
| | SP : none | |
| Oatmeal agar | G. : moderate to good, colourless | appears after 17 days |
| | Und.: beige to brown | Rectus flexibilis, some spira a and club-shaped sporangia |
| | AM. : over the whole of the colony surface, white *Wba | |
| | SP. : none | |
| Starch-mineral salts inorganic agar | G. : poor, colourless | Appears after 14 days Rectus flexibilis and few spira a (one to three spirals) |
| | Und.: colourless to brown | |
| | AM. : sparse, alabaster white, *W13 ba | |
| | SP. : none | |
| Glycerine-Asparagine agar | G. : moderate, colourless | appears after 14 days |
| | Und.: colourless to cream | Rectus flexibilis, some spira a and club-shaped sporangia |
| | AM. : over the whole of the colony surface, oyster-white, *Wb | |
| | SP. : none | |

G. : = growth
Und.: = underside
AM. : = aerial mycelium
SP. : = soluble pigments
*reference to the "Color-wheels System" Bachus, & Tresner, 1957

Physiological properties of the strain S 53210/A

| | |
|---|---|
| Nitrate reduction | negative |
| Starch hydrolysis | positive (weak) |
| Cellulose decomposition | negative |
| Tyrosine reaction | negative |
| Milk coagulation | negative |
| Milk peptonization | negative |
| Gelatine liquefaction | positive |
| Melanin formation | negative |

Carbon utilization of the strain S 53210/A

| Growth | Carbon sources |
|---|---|
| +++ | L(+)Rhamnose, D(−)Melibiose, D(+)Mannose, D(+)Maltose |
| ++ | D(+)Glucose, D(+)Galactose, D(−)Arabinose, Gycerol, Starch, D(+)Xylose, D(−)Fructose, D(−)Mannitol |
| + | D(+)Lactose, D(−)Ribose, D(−) Sorbitol,Dextrin |
| ± | D(−)Salicin, meso-Inositol, L(−)Arabinose, D(+)Melezitose, D(+)Raffinose, D(+)Saccharose |

+++ = growth and utilization good
++ = growth and utilization moderate
+ = growth and utilization poor
± = growth and utilization doubtful The cultivation of the strain S 53210/A and isolation of the antibiotics therefrom may be effected by using methods known per se for analogous strains, e.g. as in the examples.

At the start of the culture the pH value of the fermentation medium should be from 6.5 to 7.5. The optimum temperature of the culture may range between 25° to 35° C. The aeration of the culture may vary between wide limits. The maximum yield of the antibiotics may be obtained after a 4 to 7 day culture.

The production of the new antibiotics may also be effected by using suitable strains obtained, e.g. by selection or mutation of S 53210/A under the influence of ultraviolet light or X-rays, or by using other methods, e.g. by treatment of cultures with suitable chemicals, e.g. N-nitroso-N-methyl-guanidine.

As soon as a maximum amount of the antibiotics has been produced in the culture, which may e.g. be ascertained by the activity against Staphylococcus aureus, the mycelium may be separated. The antibiotics may be extracted from the culture liquor and mycelium.

The new antibiotics exhibit the following properties:

S 53210/A-I

Yellow amorphous powder M.P.>320° (decomp.) after 15 hours drying in high vacuum (0.01 to 0.1 mm Hg) at room temperature; $[\alpha]_D^{20} = +104.5°$ (c=0.637 in chloroform)

Analysis: Found C 48.8 H 4.1 N 12.04 O 19.5 S 13.7%

UV spectrum in acetonitrile, cf. in FIG. 1.

Figure 2:
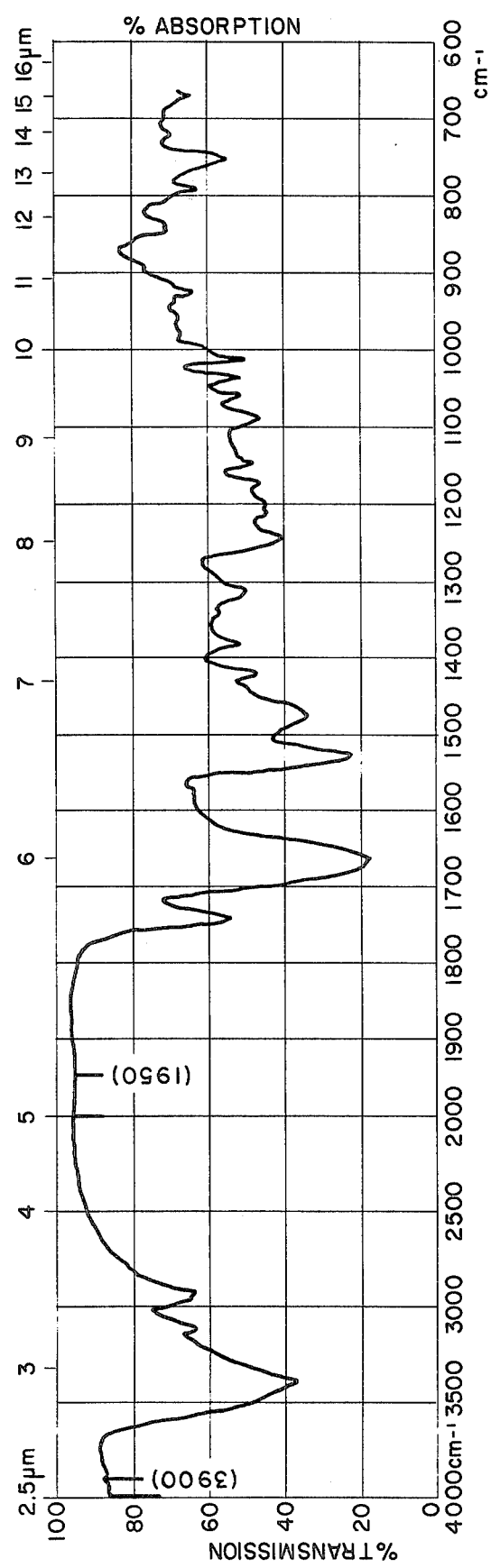

IR spectrum in KBr, cf. FIG. 2.

Figure 3:
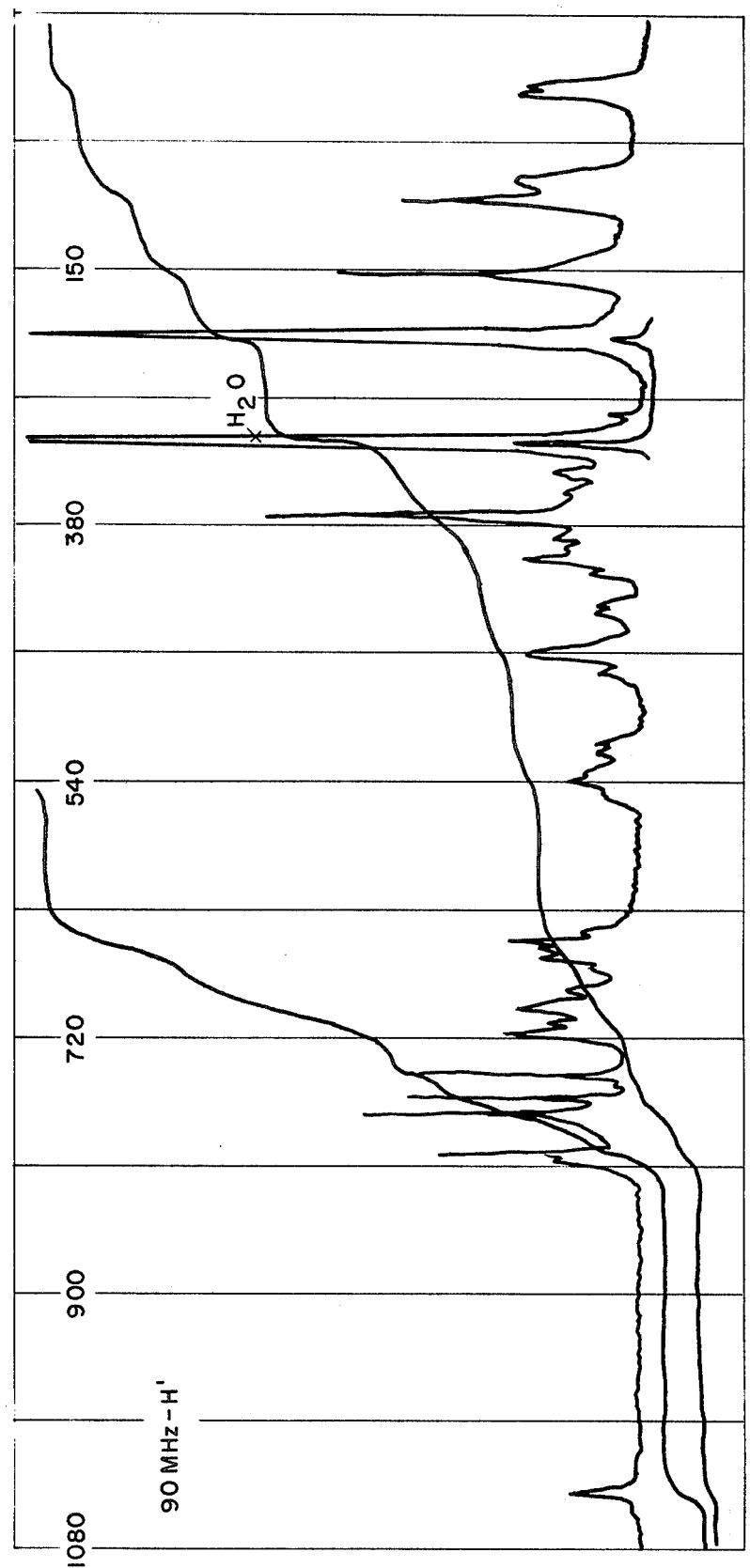

$^1$H-NMR spectrum in DMSO, 90 MHz with tetramethylsilane as internal standard, cf. FIG. 3.

Apart from unidentified amino acids, the amino acid analysis revealed an amino acid having the same retention time as threonine.

Colour reactions: Ninhydrin negative Cl$_2$-benzidine green

Colour reaction with Cl$_2$-benzidine:

The thin layer plate is sprayed with the fixing agent and is placed for 7 minutes into a chamber saturated with chlorine. After removal of the excess chlorine, the plate is sprayed.

Fixing agent: 200 ml of ethanol/acetone (1:1)+20 drops of acetic acid.

Colour solution: 0.05 M KI solution in water (1 part)+0.5% benzidine solution in 20% acetic acid (4 parts).

Solubility: S 53210/A-I is readily soluble in dimethyl formamide, acetonitrile, dioxane, dimethyl sulphoxide, scarcely soluble in chloroform, methanol, ethanol and insoluble in water and hexane.

S 53210/A-II

Yellow amorphous powder. Decomposes in sunlight. M.P.>320° (decomp.) (dried as for S 53210/A-I); $[\alpha]_D^{20} = +107.0°$ (c=0.622 in chloroform).

Analysis: Found 1st analysis C 48.8 H 4.3 N 11.9 O 19.5 S 12.5%, 2nd analysis C 51.7 H 4.9 N 11.9 O 19.3 S 12.0%.

Figure 4:
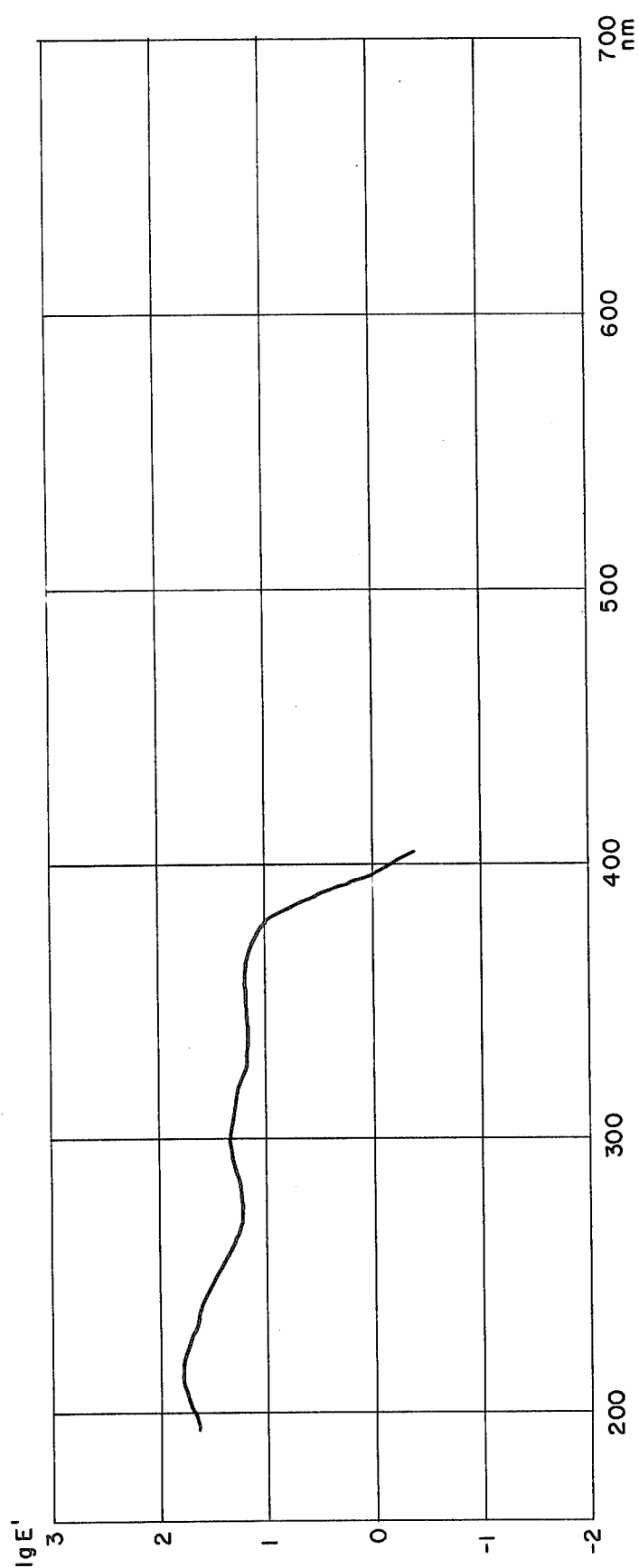

UV spectrum in acetonitrile, cf. FIG. 4.

Figure 5:
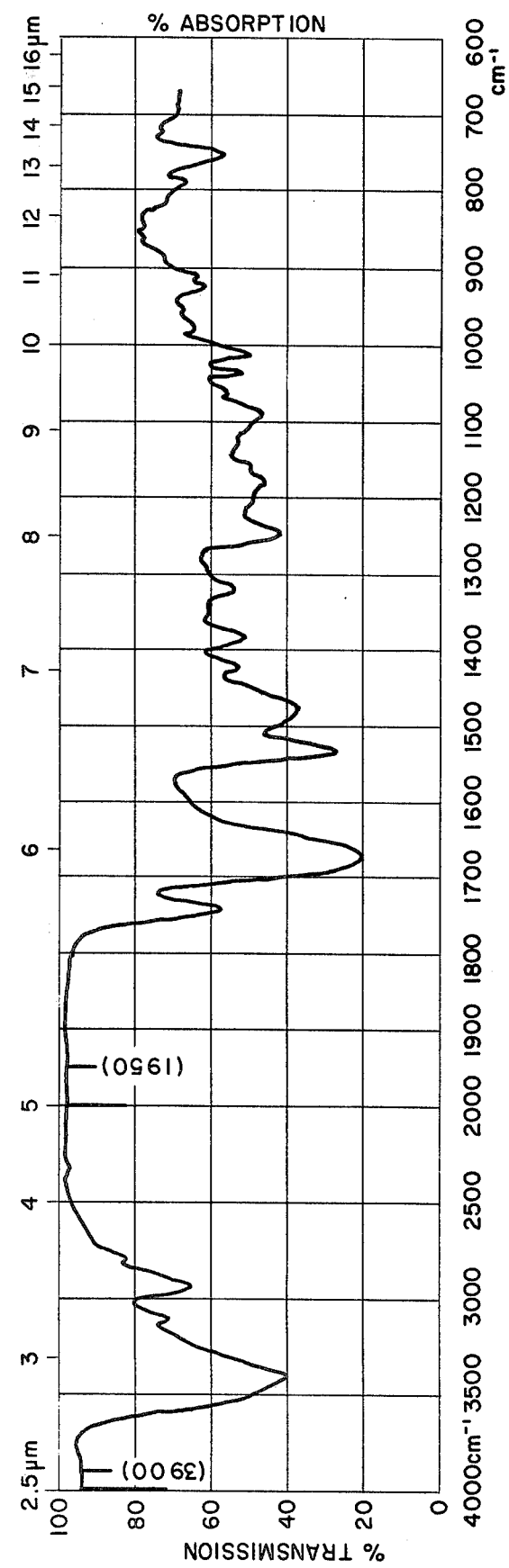

IR spectrum of KBr, cf. FIG. 5.

Figure 6:
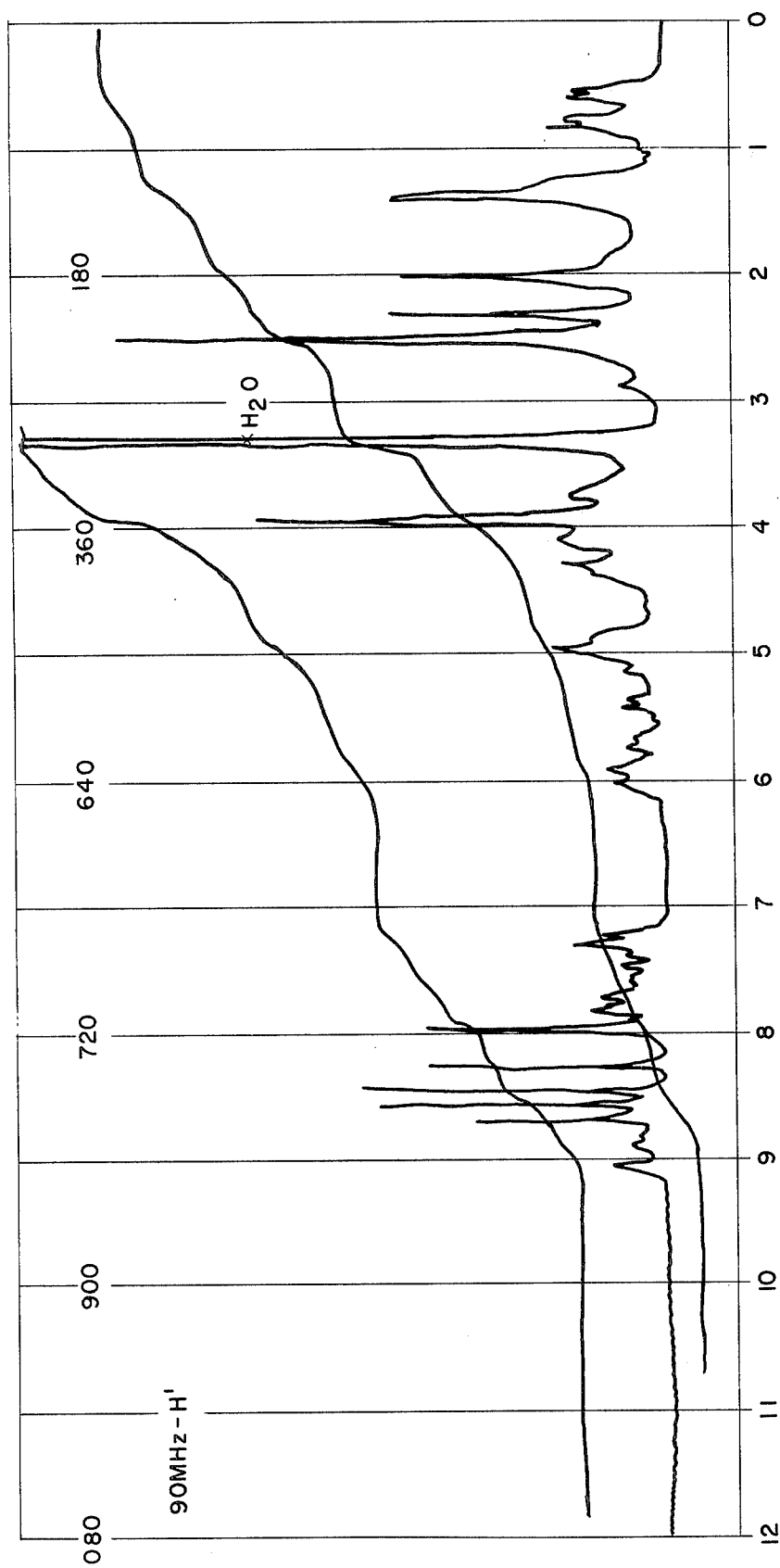

$^1$H-NMR spectrum in DMSO, 90 MHz with tetramethylsilane as internal standard, cf. FIG. 6.

$^{13}$C-NMR spectrum in DMSO using a Bruker HX-90E spectrometer at 22.6 MHz using TMS=0 ppm as internal standard, see the following table:

| $^{13}$C-NMR spektrum of S 53210/A-II 100 mg in 1.2 ml DMSO + TMS in ppm (chemical shifts relative to TMS): | |
|---|---|
| 183.53 | 95.14 |
| 171.57 | 86.50 |
| 168.32 | 80.06 |
| 167.80 | 78.31 |
| 167.60 | 70.64 |
| 163.58 | 69.40 |
| 162.86 | 68.30 |

| -continued $^{13}$C-NMR spektrum of S 53210/A-II 100 mg in 1.2 ml DMSO + TMS in ppm (chemical shifts relative to TMS): | |
|---|---|
| 161.37 | 67.45 |
| 160.85 | 66.22 |
| 160.33 | 65.57 |
| 157.79 | 64.60 |
| 154.15 | 56.02 |
| 150.84 | 55.24 |
| 150.06 | 50.75 |
| 148.69 | 44.25 |
| 145.64 | 42.50 |
| 142.91 | 34.18 |
| 134.20 | 30.41 |
| 133.94 | 26.58 |
| 133.68 | 17.87 |
| 130.43 | 15.20 |
| 129.26 | 12.86 |
| 128.03 | |
| 126.21 | |
| 125.30 | |
| 123.87 | |
| 120.68 | |
| 119.97 | |
| 113.14 | |
| 110.15 | |
| 109.63 | |
| 101.90 | |

The amino acid analysis revealed apart from unidentified amino acids an amino acid having the same retention time as threonine.

Colour reactions: Ninhydrin negative Cl$_2$-benzidine green [spray conditions as for S 53210/A-I]

Solubility: S 53210/A-II is readily soluble in chloroform, dimethyl, formamide, acetonitrile, dioxane, dimethyl sulphoxide, scarcely soluble in methanol, ethanol and insoluble in water and hexane.

S 53210/A-III

Yellow amorphous powder. Decomposes in sunlight M.P.>300° (decomp.) (dried as for S 53210/A-I) $[\alpha]_D^{20} = +67.2°$ (c=1.444 in chloroform)

Analysis: Found C 52.0 H 5.0 N 12.0 O 20.0 S 11.0%

Figure 7:
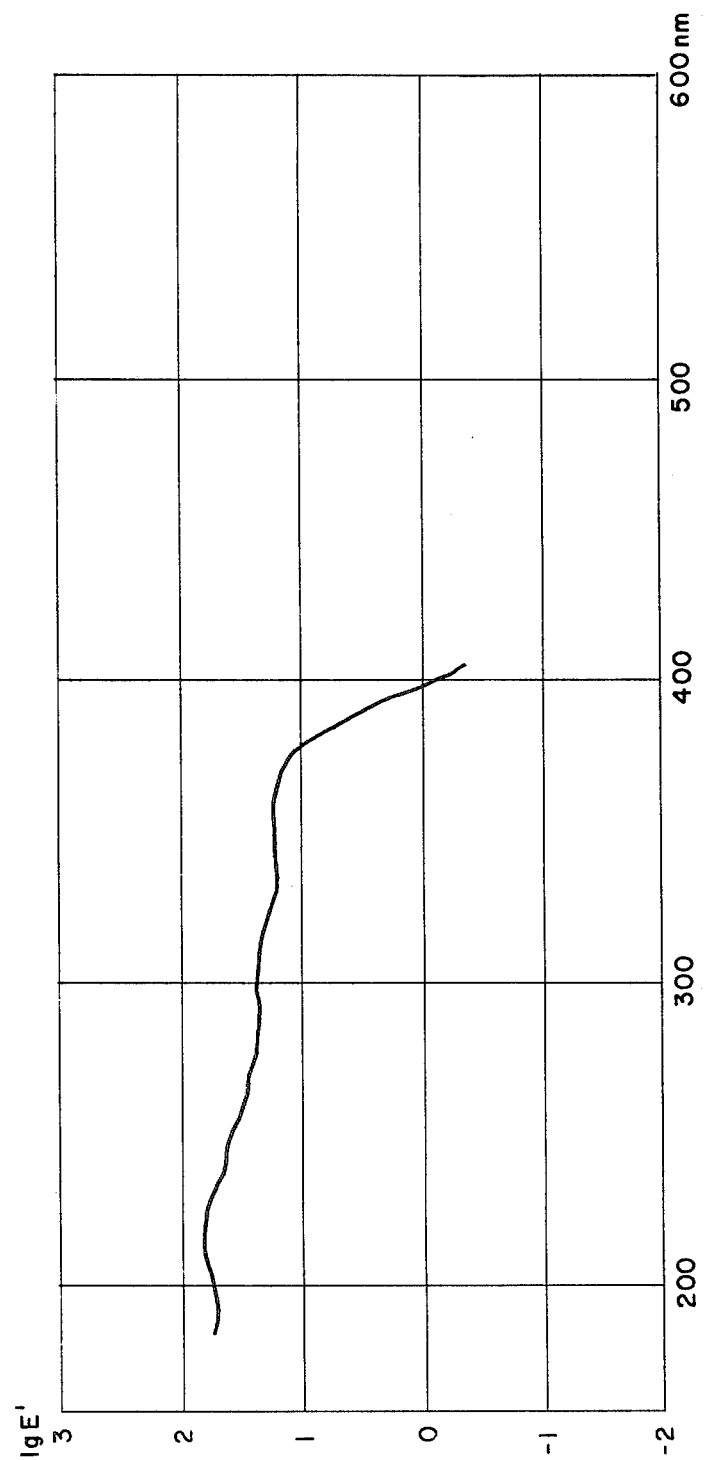

UV spectrum in acetonitrile, cf. FIG. 7

Figure 8:
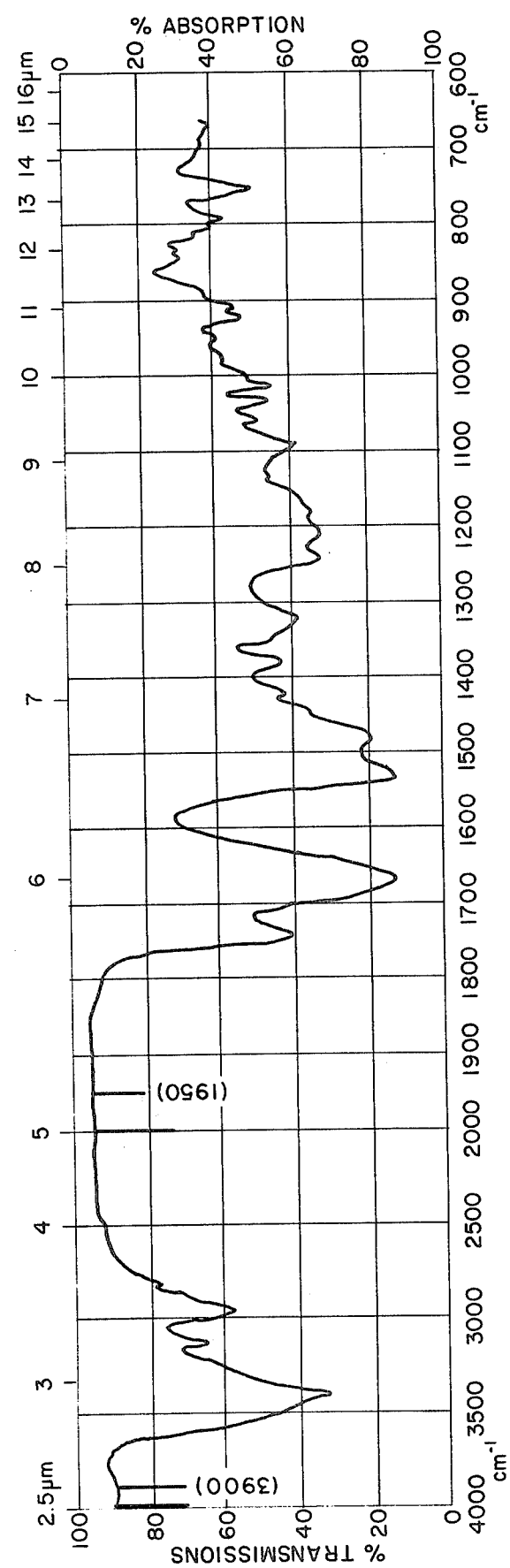

IR spectrum in KBr, cf. FIG. 8

Figure 9:
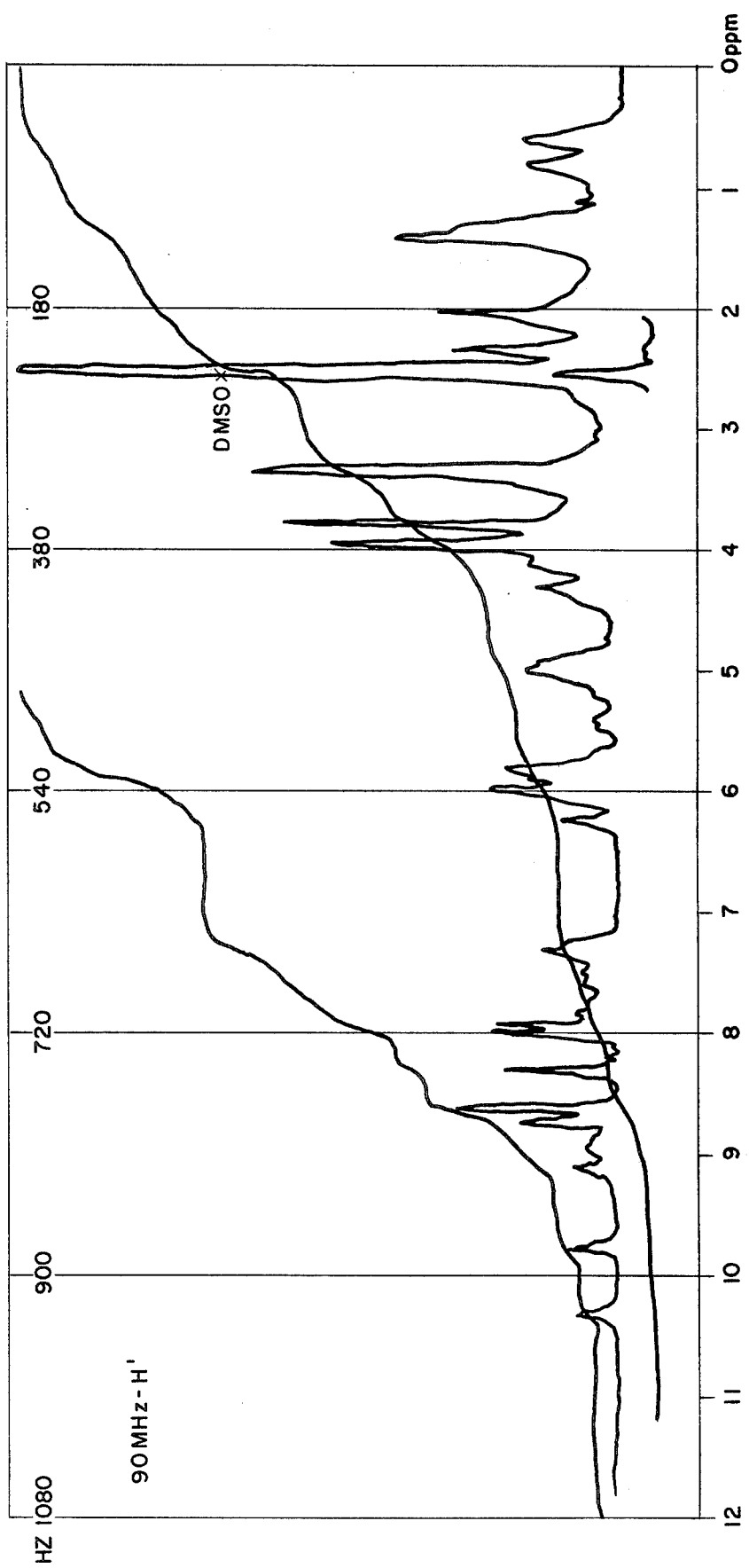

$^1$H-NMR spectrum in DMSO, 90 MHz with tetramethylsilane as internal standard, cf. FIG. 9

Apart from unidentified amino acids, the amino acid analysis revealed an amino acid having the same retention time as threonine.

Colour reaction: Ninhydrin negative Cl$_2$-benzidine green [spray conditions as for S 53210/A-I]

Solubility: S 53210/A-III is readily soluble in chloroform, dimethyl formamide, acetonitrile dioxane, dimethyl sulphoxide, scarcely soluble in methanol, ethanol and insoluble in water and hexane.

| PK determination by potentiometric titration in dimethyl sulphoxide/water (2 : 1). | | |
|---|---|---|
| S 53210/A-I | S 53210/A-II | S 53210/A-III |
| a) with 0.1 N HCl pk = 6.9 | a) with 0.1 N HCl pk$_1$ = 6.9 pk$_2$ = 5.8 | a) with 0.1 N HCl pk = 7.4 |
| b) with 0.1 N NaOH pk = 7.8 | b) with 0.1 N NaOH pk = 7.7 | b) with 0.1 N NaOH pk = 6.6 |

Table 1 shows the Rf values of the antibiotics on the thin layer chromatograms. (running distance 14 cm on silica-gel Merck 60 plates; thickness 0.25 mm)

TABLE 1

| Solvent systems: | S 53210/A-I | S 53210/A-II | S 53210/A-III | Nos-heptide (Standard) |
|---|---|---|---|---|
| $CH_2Cl_2/CH_3OH/H_2O$ (88 : 11 : 1) | 0.16 | 0.21 | 0.35 | 0.31 |
| $CH_2Cl_2/CH_3OH/H_2O$ (80 : 17.5 : 2) | 0.32 | 0.40 | 0.64 | 0.48 |
| $CH_2Cl_2/CH_3OH/H_2O$ (80 : 17.5 : 2) + 1% acetic acid | 0.22 | 0.26 | 0.36 | 0.51 |
| $CH_2Cl_2/CH_3OH/H_2O$ (80 : 17.5 : 2) + 1% Triethylamine | 0.37 | 0.45 | 0.73 | 0.51 |

Iodine may be used as the detection agent. When spraying with a 0.2% Ce $(SO_4)_2$ solution in 50% sulphuric acid and heating up to 130°, the antibiotics show a gray to brown colouration.

The antibiotics on silicagel thin layer chromatogram plates show a yellow fluorescence on exposure to ultra-violet (366 nm) light.

It will be appreciated that the above data is subject to the normal experimental error.

The antiobiotics are antimicrobially effective; they especially inhibit predominantly the growth of gram-positive bacteria. The antibiotics reveal a very wide activity towards gram-positive bacteria, but not against yeast and fungi.

The effect also covers the pathogenic representatives of the gram-positive bacteria, such as staphylococcae, streptococcae, corynebacteria, mycobacteria. The new antibiotics are also effective against mycoplasmas and Neisseria.

The following minimum inhibition concentrations (mcg/ml) were found in the series dilution test:

| Organism: | MIC S 53210/A-I | MIC S 53210/A-II | MIC S 53210/A-III |
|---|---|---|---|
| Staphylococcus aureus | 0.01 | 0.01 | 0.01 |
| S. aureus res. Penicillin | 0.01 | 0.01 | 0.01 |
| S. aureus res. Tetracycline | 0.01 | 0.01 | 0.1 |
| S. aureus res. Rifamycin | 0.01 | 0.01 | 0.01 |
| S. aureus 6538 P | 1.0 | 0.3 | 0.03 |
| Streptococcus faecalis res. Aminoglycosides | 0.01 | 0.01 | 0.3 |
| Streptococcus pyogenes | 0.01 | 0.1 | 0.3 |
| Streptococcus faecalis | 0.1 | 0.3 | 0.3 |
| Streptococcus haemolyticus | 0.01 | 0.01 | 0.01 |
| Diplococcus pneumoniae | 0.1 | 0.1 | 0.3 |
| Corynebacterium equi | 0.03 | 0.1 | 0.3 |
| Sarcina lutea res. Erythromycin | 0.01 | 0.01 | 0.3 |
| Bacillus subtilis | 0.3 | 0.1 | 1.0 |
| Clostridium sphenoides | 1.0 | 0.3 | 1.0 |
| Clostridium pasteurianum | 0.1 | 0.1 | 0.03 |
| Mycobacterium thamnophesos | 0.03 | 0.03 | 0.3 |
| Mycobacterium smegmatis | 0.01 | 0.03 | 0.3 |
| Mycoplasma laidlawii | 0.1 | 0.1 | 3.2 |
| Mycoplasma gallisepticum | 1.0 | 1.0 | 3.0 |
| Neisseria catharalis | 0.1 | 0.3 | 0.3 |
| Neisseria pharyngis | 0.01 | 0.01 | 0.1 |

Medium Brain Heart Infusion Broth, inoculum density $10^5$ germs/ml, incubation temperature 37°, incubation time 24 hours.

The effect is also observed in vivo on parenteral administration of from 0.2 to 300 mg/kg animal body weight of the compound.

As indicated in the above results, the antibiotics also exhibit activity against certain gram negative bacteria in a concentration of from 0.12 to 5 μg/ml., and also against chlamydia strains at a concentration of 0.005 μg/ml.

The compounds are therefore useful as antibiotics. For the above mentioned use the dosage will, of course, vary depending on the compound employed, mode of administration and therapy desired. However, in general, satisfactory results are obtained when administered at a daily dosage of from 0.1 mg to about 1 mg per kg animal body weight, conveniently given in divided doses 2 to 4 times a day or in sustained release form. For the larger mammal, the total daily dosage is in the range from about 10 to about 50 mg, and dosage forms suitable for oral administration comprises from about 2.5 mg to about 25 mg of the compounds admixed with a solid or liquid pharmaceutical carrier or diluent.

The compounds may be administered alone, in the form of a pharmaceutical composition or mixed with animal feed. The present invention therefore provides a pharmaceutical composition comprising S 53210/A-I, S 53210/A-II or S 53210/A-III in association with a pharmaceutical carrier or diluent. Such compositions may be formulated in conventional manner to be for example a solution or a tablet. The present invention also comprises an animal feed incorporating S 53210/A-I, S 53210/A-II or S 53210/A-III, preferably in a concentration of from 1 to 500 mg per kg of feed.

The acute toxicities of the antibiotics were determined in the mouse over 7 days. Results obtained are as follows:

| Compound | $LD_{50}$ (mg/kg) | Administration route |
|---|---|---|
| S 53210/A-I | >100 | i.p. |
| S 53210/A-II | >300 | i.p. |
|  | >100 | i.v. |
| S 53210/A-III | >300 | i.p. |
| Thiostrepton (standard) | <100 | i.v. |

In the following Examples all temperatures are indicated in degrees Centigrade.

All parts are by volume unless otherwise specified.

EXAMPLE 1: Fermentation of the strain S 53210/A in shaken cultures (a) Agar starting culture The agar culture of the strain S 53210/A used as starting material is obtained by inoculating a culture medium (I) of the following composition:

| | g/liter |
|---|---|
| Cerelose (glucose) | 4.0 |

-continued

|  | g/liter |
|---|---|
| Malt extract | 10.0 |
| Yeast extract | 4.0 |
| Agar (bacto) | 20.0 |
| distilled water | 1 liter | with a spore suspension of the originally isolated strain S 53210/A produced in a manner known per se. The medium is adjusted to pH 8.3 to 8.6 with NaOH before sterilisation and has a pH 6.9 to 7.3 (20 minutes at 120°) after sterilisation.

(b) Spore suspension

To a well sporulating agar starting culture of the strain S 53210/A there are added 5 ml of sterile, 0.9% common salt solution yielding a dense spore and mycelial suspension.

(c) Precultures 1 ml of the spore suspension is used for the inoculation of a 200 ml Erlenmeyer flask containing 50 ml of the following preculture medium (II):

|  | g/liter |
|---|---|
| Dextrin | 10.0 |
| Glucose | 10.0 |
| Peptone | 5.0 |
| Yeast extract | 5.0 |
| $CaCO_3$ | 1.0 |
| distilled water | 1 liter |

The pH value is adjusted with NaOH to 7.2. The preculture medium is sterilised in an autoclave at 120° for 20 minutes with the end pH value from 7.0 to 7.2. The thus treated preculture is aerobically incubated for 3 days at 27° on a rotary mechanical shaker (220 rotations/minute) and is used for the inoculation of a second preculture by inoculating 5 ml of the first preculture in a 500 ml Erlenmeyer flask with 100 ml of the following medium (III):

|  | g/liter |
|---|---|
| Meat extract | 3.0 |
| Tryptone | 5.0 |
| Glucose | 1.0 |
| Soluble starch | 24.0 |
| Yeast extract | 5.0 |
| $CaCO_3$ | 2.0 |
| distilled water | 1 liter |

The pH value is adjusted to 7.2 with NaOH and the medium is sterilised in an autoclave at 120° during 20 minutes, whereupon the end pH value is 7.0 to 7.2.

(d) Fermentation culture

The second preculture is aerobically incubated for 3 days at 27° on a rotary mechanical shaker (220 r.p.m.) and is then used directly for inoculation of a fermentation medium by inoculating 5 ml of the second preculture to a 500 ml Erlenmeyer flask with 100 ml of the following medium (IV):

|  | g/liter |
|---|---|
| Malt extract | 30.0 |
| Blood peptone | 7.5 |
| distilled water | 1 liter |

The pH value is adjusted to 7.0 with NaOH and the medium is sterilised in an autoclave at 120° during 20 minutes, whereupon the pH value reaches 6.8 to 7.0. The thus prepared fermentation culture is incubated during 5 days at 27° on a rotary mechanical shaker (220 r.p.m.).

EXAMPLE 2: Cultivation of the strain S 53210/A in a fermenter (a) The starting culture for the growing of a 500 liter fermentation mixture is an agar slant culture of the originally isolated strain S 53210/A cultivated for 14 days at 27° on a culture medium (I). 6 2-L-Erlenmeyer flask each containing 1 liter of culture medium (II) are inoculated with 60 ml of spore and mycelial suspension from 3 agar slant cultures. This preculture is incubated for 7 days on a rotary mechanical shaker at 27° at 180 r.p.m.

The intermediate culture in a 75 liter steel fermenter (50 liters fermentation volume) is inoculated with the preculture from the 6 Erlenmeyer flasks. The medium of this culture stage contains culture medium (III). The incubation is effected for 3 days at 27° at an aeration rate of 0.7 L V/V/min and at 0.5 bar pressure and at 200 rpm.

The main fermentation in a 750 liter fermentation vessel (500 liter fermentation volume) is effected at 27° with a nutrient solution of the following composition per liter: 30 g of malt extract, 7.5 g of blood peptone, 1 mg of $FeSO_4.7H_2O$, 1 mg of $MnCl_2.4H_2O$, 1 mg of $ZnSO_4.7H_2O$ and demineralised water. The incubation lasts 6 days stirring at 130 r.p.m. with an aeration rate of 0.7 L V/V/min and at 0.5 bar pressure. The pH end value is 8.7 to 8.9 (further working up see Example 3).

(b) The starting culture for growing a 500 liter fermentation culture is a stationary culture (Erlenmeyer flask of 500 ml with 100 ml of agar) of the originally isolated strain S 53210/A. This culture with the agar medium containing per liter 20 g of agar, 20 g of malt extract, 4 g of yeast extract and demineralised water, is incubated for 14 days at 33°. 200 ml of a spore and mycelial suspension from 2 stationary cultures are used for inoculation of 1 glass fermenter containing 10 liters of a nutrient solution of the following composition: 20 g of glucose, 5 g of peptone, 5 g of yeast extract, 1 g of $CaCO_3$ and demineralised water to 1 liter. This preculture is incubated for 4 days at 30° with an aeration rate of 0.7 liters V/V/min and stirring at 250 rpm. The intermediate culture in a 75 liter steel fermenter (50 liters fermenting volume) is inoculated with 7 liters of the preculture The medium has the same composition as the preculture: 20 g of glucose, 5 g of peptone, 5 g of yeast extract, 1 g of $CaCO_3$ and demineralised water add 1 liter. The incubation is effected for 3 days at 30° at an aeration rate of 0.7 liters V/V/min at 0.5 bar pressure and stirring at 200 rpm.

The main fermentation in a 750 liter fermentation vessel (500 liters of fermentation volume) is effected at 30° with a nutrient mixture of the following composition: per liter 30 g of malt extract, 7.5 g of blood peptone, 1 mg of $FeSO_4.7H_2O$, 1 mg of $MnCl_2.4H_2O$, 1 mg of $ZnSO_4.7H_2O$ and demineralised water. The incubation lasts for 4 days of stirring at 130 rpm and aerating at 0.7 liters V/V/min and at 0.5 bar pressure. The pH end value is 7.8. (further working up see Example 4).

EXAMPLE 3: Isolation of S 53210/A-I and S 53210/A-II 420 liters of fermentation broth (example 2a) are adjusted to pH 7 with 20% sulphuric acid and are separated with a Westfalia separator whereupon 400 liters of culture filtrate and 15 kg of mycelium are obtained. The culture filtrate is extracted three times with 300 liters of n-butanol. Upon washing of the extracts with 100 liters of water, the organic phase is concentrated by evaporation to dryness at 20° to 50° concentrate temperature, whereupon 315 g of crude extract result.

The mycelium is three times extracted after homogenization with 60 liters of methanol during 30 mintues. The methanolic extracts obtained upon filtration by suction of the solid substance, are combined and are concentrated by evaporation to approximately 40 liters by the addition of water on a circulation evaporizer. The aqueous phase is then extracted four times each with 40 liters of n-butanol and the extracts are washed with 20 liters of water. The combined extracts are concentrated by evaporation to dryness as above (77 g of crude extract).

392 g of combined butanol extracts obtained from culture filtrate and mycelium are then treated with 500 ml of water and are extracted three times each with 1 liter of methylene chloride/isopropanol (7:3). The organic phases are combined and yield 188 g of material upon concentration by evaporation in a vacuum at 40°. This material is dissolved in methylene chloride/methanol (1:1) and is mixed with 400 g of silica gel and, upon evaporation of the solvent, the powder is brought onto a column of 1 kg of silica gel (Merck, grain size 0.063–0.2 mm) prepared with methylene chloride. The elution is effected at first with methylene chloride and methylene chloride by the addition of 3 to 5% of methanol and then with methylene chloride/methanol/water (88:11:1). Finally washing is effected with methylene chloride/methanol (1:1). 65.5 g of fractions are obtained containing the active antibiotics S 53210/A-I and S 53210/A-II as mixture with by-products.

This material is dissolved in methanol and the solution is brought onto a column of 1.5 kg of Sephadex LH 20 prepared with methanol. The elution with methanol yields 6.9 g of fractions with activity against Staphylococcus aureus. The subsequent chromatography of this material on a column of 50 g of silica gel prepared with methylene chloride/acetone (2:1) and elution with methylene chloride/acetone (2:1) and then with methylene chloride/methanol (1:1) yields an enriched fraction of S 53210/A-I and S 53210/A-II. The fraction is rechromatographed on a column of 400 g of silica-gel (Merck, grain size 0.040–0.063 mm) prepared with methylene chloride/methanol/water (88:11:1). The continuous elution with methylene chloride/methanol/water (88:11:1) yields 963 mg of active material which is dissolved in 35 ml of methylene chloride. Upon the addition of 35 ml of methanol and concentration by evaporation to approximately half the volume a precipitation occurs, whereupon a mixture of S 53210/A-I and S 53210/A-II is obtained as amorphous powder. In order to separate the two antibiotically active metabolites the mixture is chromatographed on 400 g of silica-gel in analogous manner as described above, whereupon at first S 53210/A-II and then S 53210/A-I is eluted. The fractions containing S 53210/A-II are dissolved in methylene chloride/methanol (1:1), whereupon after concentration by evaporation the metabolite S 53210/A-II precipitates as amorphous yellow powder. M.P. >320° after drying for 15 hours in a high vacuum at room temperature. The fractions containing S 53210/A-I yield S 53210/A-I as yellow amorphous powder upon an analogous precipitation from methylene chloride/methanol (1:1). M.P. >320° after drying for 15 hours in a high vacuum at room temperature. The purity test of the chromatography fractions is effected by thin layer chromatography on silica gel plates with the solvent methylene chloride/methanol/water (80:17.5:2). The active fractions are tested by using Staphylococcus aureus and Streptococcus faecalis.

EXAMPLE 4: Isolation of S 53210/A-III 500 liters of culture broth (see example 2b) are adjusted to pH 7 with 2 N sulphuric acid, 500 liters of ethyl acetate are added and are homogenized for 90 minutes with a Dispax reactor. The separation of the organic phase is effected with a Westfalia separator. After washing with 100 liters of water, the extract is concentrated by evaporation to dryness in a vacuum at 20° to 40° concentrate temperature (146 g of crude extract). A repeated extraction yields 51 g of crude extract.

The 197 g of combined extracts are added with stirring to 2 liters of hexane. The supernatant solution is decanted off and the oily residue is liberated from the solvent in a vacuum at 50°, whereupon 80.2 g of precipitation product with activity against Staphylococcus aureus are yielded. This material is dissolved in chloroform/methanol (1:1) and the solution is brought onto a column of 1 kg of Sephadex LH$_{20}$ prepared with chloroform/methanol (1:1). The elution with chloroform/methanol (1:1) yields 14.5 g of fractions containing S 53210/A-III. The latter are dissolved in methylene chloride +3% methanol and the solution is brought onto a column of 250 g of silica-gel Merck (grain size 0.063–0.2 mm) prepared with methylene chloride +3% methanol. The elution is at first effected with methylene chloride by the addition of 3 to 5% methanol, and then with methylene chloride +10% methanol. 4.8 g of enriched fractions of S 53210/A-III are obtained. The fractions are dissolved in 25 ml of methylene chloride and are concentrated by evaporation at room temperature upon the addition of 50 ml of methanol, whereupon S 53210/A-III precipitates. The substance is filtered off and is washed with methanol and ether. S 53210/A-III is obtained as amorphous yellow powder. M.P. >300° after drying for 15 hours in a high vacuum at room temperature.

The purity test of the chromatographic fractions with an activity against Staphylococcus aureus is effected by thin layer chromatography on silica gel with methylene chloride/methanol/water (88:11:1) and methylene chloride/methanol/water (92:7.5:0.5) as solvent.

EXAMPLE 5

In analogous manner to Examples 4 and 5 the antibiotics S 53210/A-I, S 53210/A-II and S 53210/A-III may be obtained from the culture broth of Example 1.

What we claim is:

1. A compound selected from the group consisting of:
(1) S 53210/A-I having a UV spectrum in acetonitrile as shown in FIG. 1, an IR spectrum in KBr as shown in FIG. 2, an $^1$H-NMR spectrum in DMSO at 90 MHz with tetramethylsilane as internal standard as shown in FIG. 3 and an elementary analysis of C 48.8%, H 4.1%, N 12.4%, O 19.5%, S 13.7%, (2) S 53210/A-II having a UV spectrum in acetonitrile as shown in FIG. 4, an IR spectrum in KBr as shown in FIG. 5 and $^1$H-NMR spectrum in DMSO at 90 MHz with tetramethylsilane as internal standard as shown in FIG. 6 and an elementary analysis of C 48.8%, H 4.3%, N 11.9%, O 19.5%, S 12.5%; and (3) S 53210/A-III having a UV spectrum in acetonitrile as shown in FIG. 7, an IR spectrum in KBr as shown in FIG. 8, an $^1$H-NMR spectrum in DMSO at 90 MHz with tetramethylsilane as internal standard as shown in FIG. 9 and an elementary analysis of C 52.0%, H 5.0%, N 12.%, O 20.0%, S 11.0%.

2. The compound of claim 1 which is S 53210/A-I.

3. The compound of claim 1 which is S 53210/A-II.

4. The compound of claim 1 which is S 53210/A-III.

5. A process for the production of a compound of claim 1 which comprises cultivating the strain of *Microcellobosporia brunea,* nov. Sp. King NRRL 11,122 under aerobic fermentation conditions in a nutrient medium until a sufficient amount of S 53210/A-I; S 53210/A-II or S 53210/A-III is produced.

6. A pharmaceutical composition or animal feed for combatting bacteria comprising an anti-bacterial effective amount of a compound of claim 1 in association with a pharmaceutical carrier or diluent.

7. A method of combatting bacteria in animals which comprises administering to said animals an anti-bacterial effective amount of a compound of claim 1.

* * * * *

UNITED STATES PATENT AND TRADEMARK OFFICE
CERTIFICATE OF CORRECTION

PATENT NO. : 4,216,206
DATED : August 5, 1980
INVENTOR(S) : CAMILLA KELLER-JUSLEN; HAMILTON D. KING It is certified that error appears in the above—identified patent and that said Letters Patent is hereby corrected as shown below:

Claim 5, Col. 12, line 4, delete "crocellobosporia" and insert in its place --croellobosporia-- .

Signed and Sealed this

Twenty-fourth Day of July 1984

[SEAL]

Attest:

GERALD J. MOSSINGHOFF

Attesting Officer

Commissioner of Patents and Trademarks